US010441178B2

(12) United States Patent
Campo et al.

(10) Patent No.: US 10,441,178 B2
(45) Date of Patent: Oct. 15, 2019

(54) MONITORING DEVICE WITH VOLATILE ORGANIC COMPOUNDS SENSOR AND SYSTEM USING SAME

(71) Applicants: David Campo, Boulogne Billancourt (FR); Stéphane Carpentier, Hong Kong (CN); Amaury Dumoulin, Neuilly sur Seine (FR); Nadine Buard, Meudon (FR); Eric Carreel, Meudon (FR)

(72) Inventors: David Campo, Boulogne Billancourt (FR); Stéphane Carpentier, Hong Kong (CN); Amaury Dumoulin, Neuilly sur Seine (FR); Nadine Buard, Meudon (FR); Eric Carreel, Meudon (FR)

(73) Assignee: WITHINGS, Issy les Moulineaux (FR)

(*) Notice: Subject to any disclaimer, the term of this patent is extended or adjusted under 35 U.S.C. 154(b) by 362 days.

(21) Appl. No.: 14/805,063

(22) Filed: Jul. 21, 2015

(65) Prior Publication Data

US 2016/0015278 A1 Jan. 21, 2016

(30) Foreign Application Priority Data

Jul. 21, 2014 (FR) ...................... 14 56996

(51) Int. Cl.
*H04N 7/00* (2011.01)
*A61B 5/0205* (2006.01)
(Continued)

(52) U.S. Cl.
CPC .......... *A61B 5/0205* (2013.01); *A61B 5/0004* (2013.01); *A61B 5/02416* (2013.01);
(Continued)

(58) Field of Classification Search
CPC ............ G01N 27/327; G01N 33/0075; G01N 33/497; G01N 27/407; G08B 21/12;
(Continued)

(56) References Cited

U.S. PATENT DOCUMENTS 6,679,830 B2* 1/2004 Kolarovic .............. A61G 11/00
600/22
7,611,472 B2* 11/2009 Lu ........................... A61B 5/09
600/538
(Continued)

FOREIGN PATENT DOCUMENTS

CN 102309315 A 1/2012
WO WO 2013/093686 A1 6/2013
(Continued)

OTHER PUBLICATIONS

Search report for related French Application No. 14 56996; report dated Mar. 26, 2015.
(Continued)

*Primary Examiner* — Frank F Huang
(74) *Attorney, Agent, or Firm* — Miller, Matthias & Hull LLP

(57) ABSTRACT

Video monitoring device comprising a computing unit, a camera, a communication interface, and a volatile organic compounds sensor configured to measure at least a concentration of organic compounds in a room of interest, said computing unit being configured to record the concentrations of organic compounds reported by the volatile organic compounds sensor, and configured to send images taken by the camera and volatile organic compounds concentrations to a remote entity, such as a smartphone over a wireless link.

11 Claims, 5 Drawing Sheets

(51) Int. Cl.
*A61B 5/00* (2006.01)
*A61B 5/024* (2006.01)
*A61B 5/08* (2006.01)
*G01N 33/00* (2006.01)
*H04N 7/18* (2006.01)
*A61B 5/11* (2006.01)
*G06T 7/00* (2017.01)
*G06K 9/00* (2006.01)
*G06K 9/32* (2006.01)
*G06T 7/73* (2017.01)

(52) U.S. Cl.
CPC .......... *A61B 5/0816* (2013.01); *A61B 5/1128* (2013.01); *A61B 5/7207* (2013.01); *G01N 33/0047* (2013.01); *G06K 9/0053* (2013.01); *G06K 9/3233* (2013.01); *G06T 7/0016* (2013.01); *G06T 7/75* (2017.01); *H04N 7/185* (2013.01); *A61B 2503/04* (2013.01); *A61B 2560/0242* (2013.01); *G06T 2207/10024* (2013.01); *G06T 2207/10048* (2013.01); *G06T 2207/30076* (2013.01); *G06T 2207/30201* (2013.01)

(58) Field of Classification Search
CPC .. A61F 13/42; A61F 2013/424; A61B 5/6891; A61B 5/6889
See application file for complete search history.

(56) References Cited

U.S. PATENT DOCUMENTS

| | | | | |
|---|---|---|---|---|
| 7,872,670 | B2* | 1/2011 | Kikuchi | H04N 5/23212 348/157 |
| 8,094,013 | B1 | 1/2012 | Lee | |
| 9,674,323 | B1* | 6/2017 | Yu | H04M 1/0274 |
| 2004/0249290 | A1* | 12/2004 | Shani | A61B 5/0059 600/476 |
| 2005/0027336 | A1* | 2/2005 | Nemenov | A61B 5/0059 607/98 |
| 2005/0212950 | A1* | 9/2005 | Kanai | H04N 5/23212 348/345 |
| 2006/0139707 | A1* | 6/2006 | Kimura | H04N 1/62 358/518 |
| 2007/0217199 | A1* | 9/2007 | Adam | A61N 5/0616 362/276 |
| 2008/0120577 | A1* | 5/2008 | Ma | G06F 3/0325 715/863 |
| 2008/0136958 | A1* | 6/2008 | Nakahara | G06K 9/00255 348/345 |
| 2008/0294012 | A1* | 11/2008 | Kurtz | A61B 5/0059 600/300 |
| 2010/0322300 | A1* | 12/2010 | Li | G06K 9/00234 375/240.01 |
| 2012/0220969 | A1* | 8/2012 | Jang | A61F 13/42 604/361 |
| 2014/0155759 | A1* | 6/2014 | Kaestle | A61B 5/0077 600/479 |
| 2014/0180132 | A1 | 6/2014 | Shan et al. | |
| 2015/0212034 | A1* | 7/2015 | Ansley | G01N 33/0075 204/403.01 |
| 2015/0230863 | A1* | 8/2015 | Youngquist | A61B 18/203 606/9 |
| 2015/0330958 | A1* | 11/2015 | Carney | A61F 13/42 73/23.34 |

FOREIGN PATENT DOCUMENTS

WO WO 2013/164724 A1 11/2013
WO WO 2013/166341 A1 11/2013
WO WO 2013/170035 A1 11/2013

OTHER PUBLICATIONS

Fang Zhou et al: "Remote Measurements of Heart and Respiration Rates for Telemedicine", Plos One, vol. 8, No. 10, Oct. 8, 2013 (Oct. 8, 2013), p. e71384, XP055140268, D01; 10.1371/journal.pone. 0071384 *abrégé; figures 6a,7 * sections; "introduction", "system set-up", "measurement methodology", discussion*.

N. Bouaynaya et al: "<title>A complete system for head tracking using motion-based particle filter and randomly perturbed active contour</title>" Proceedings of SPIE, vol. 5685, Mar. 14, 2005 (Mar. 14, 2005), pp. 864-873, XP055179273, ISSN: 0277-786X, DOI: 10.1117/12.587244 * titre, section "motivation"; figure 2.

* cited by examiner

MONITORING DEVICE WITH VOLATILE ORGANIC COMPOUNDS SENSOR AND SYSTEM USING SAME

CROSS-REFERENCE TO RELATED APPLICATION

This application claims priority under the Paris Convention to French Patent Application No. 14 56996 filed on Jul. 21, 2014.

FIELD OF THE DISCLOSURE

Background of the Disclosure

The present invention relates to video monitoring devices and methods. For example, such video monitoring devices and methods can be used to monitor a baby sleeping in its crib, with optionally an interaction between the baby and its parent or caregiver, either an audio interaction or a video/audio interaction.

More specifically, it is known in the art a method and device for monitoring certain vital signs of the baby, in particular the heart rate and respiratory rate.

U.S. Pat. No. 8,094,013 and WO2013170035 disclose devices of this type.

However, the need to improve such known devices and more generally to improve general purpose indoor video monitoring devices/systems has been identified by the inventors.

The present invention is intended to overcome at least some of the disadvantages of the prior art.

SUMMARY OF THE DISCLOSURE

To this end, it is proposed a video monitoring device comprising a computing unit, a camera, a communication interface, and a volatile organic compounds sensor configured to measure at least a concentration of organic compounds in a room of interest, said computing unit being configured to record the concentrations of organic compounds reported by the volatile organic compounds sensor, and configured to send images taken by the camera and volatile organic compounds concentrations to a remote entity, such as a smartphone over a wireless link.

With these arrangements, video surveillance can be advantageously complemented by remote surveillance of air quality in a room. Also, images and VOC levels can be analyzed in correlation.

It is noted that volatile organic compounds is called in short 'VOC'.

In various embodiments of the above invention, one or more of the following arrangements may possibly be used.

the volatile organic compounds sensor (37) is configured to detect multiple organic gases, such as butane, propane, octane, methanol, ethanol, propanol, butanol, and even aromatic compounds such as benzene, ethylbenzene, and toluene; most usual gases that are nocive or at least not particularly healthy to breathe, that may be present in a room of a home, can be detected;

the volatile organic compounds sensor is configured to detect H2S; this allows detection of something with is decomposing or rotting in the room;

the volatile organic compounds sensor can be complemented by a humidity sensor to compensate for water vapour in air; improving accuracy;

the computing unit can store successive organic compound concentration level values in memory, for transmission at regular intervals to the remote entity; this decreases the load on wireless network;

an alert threshold can be provided in the computing unit, which allows to send immediately to the smartphone an alert message, as soon as the VOC concentration exceeds the predetermined alert threshold;

the VOC sensor can be an ion detector using photoionization of the molecules in an air sample collected in the room of interest;

the VOC sensor can be an electrochemical MOS on-chip sensor using oxidation-reduction reactions with gas(es) present in ambient air, to assess VOC concentration level; this facilitates integration of the sensor in the device;

the VOC sensor provides an aggregate level of organic compounds which combines all the organic compounds present in the air of the room.

Some vital signs of a baby, such as the heart rate (HR) and/or respiratory rate (RR) of the baby are evaluated by photoplethysmographic analysis of the captured images, thereby the video monitoring device forms a device suitable for monitoring a baby in a room or in a crib; a correlation between on one hand VOC levels and on the other hand heart rate (HR) and/or respiratory rate (RR) can be assessed; R8 The video monitoring device may comprise a loudspeaker and a microphone, thereby forming two-way audio link, particularly suitable for interacting with a baby in a room or in a crib, remotely from a parent/caretaker using the smartphone.

The invention also relates to a system comprising a monitoring device as described above and a smartphone.

The invention also relates to a method to monitor events in a room and an air quality in the room, the method comprising:
measuring a concentration of organic compounds in a room with a volatile organic compounds sensor,
taking images of at least part of the room,
storing the organic compound concentration data in a memory of a computing unit,
send images taken by the camera and volatile organic compounds concentrations, from the computing unit to a remote entity such as a smartphone over a wireless link.

In addition, optionally, the transmission to the smartphone may occur at regular intervals.

In addition, optionally an alert threshold may be provided in the computing unit, the method further comprising:
sending quickly to the smartphone an alert message, as soon as the VOC concentration exceeds the predetermined alert threshold.

BRIEF DESCRIPTION OF THE DRAWINGS

Other features, objects, and advantages of the invention will be apparent from reading the following description of an embodiment of the invention, given by way of non-limiting example. The invention will also be better understood by referring to the accompanying drawings, in which.

DETAILED DESCRIPTION OF THE DISCLOSURE

In the various figures, the same references designate identical or similar elements.

Figure 1:
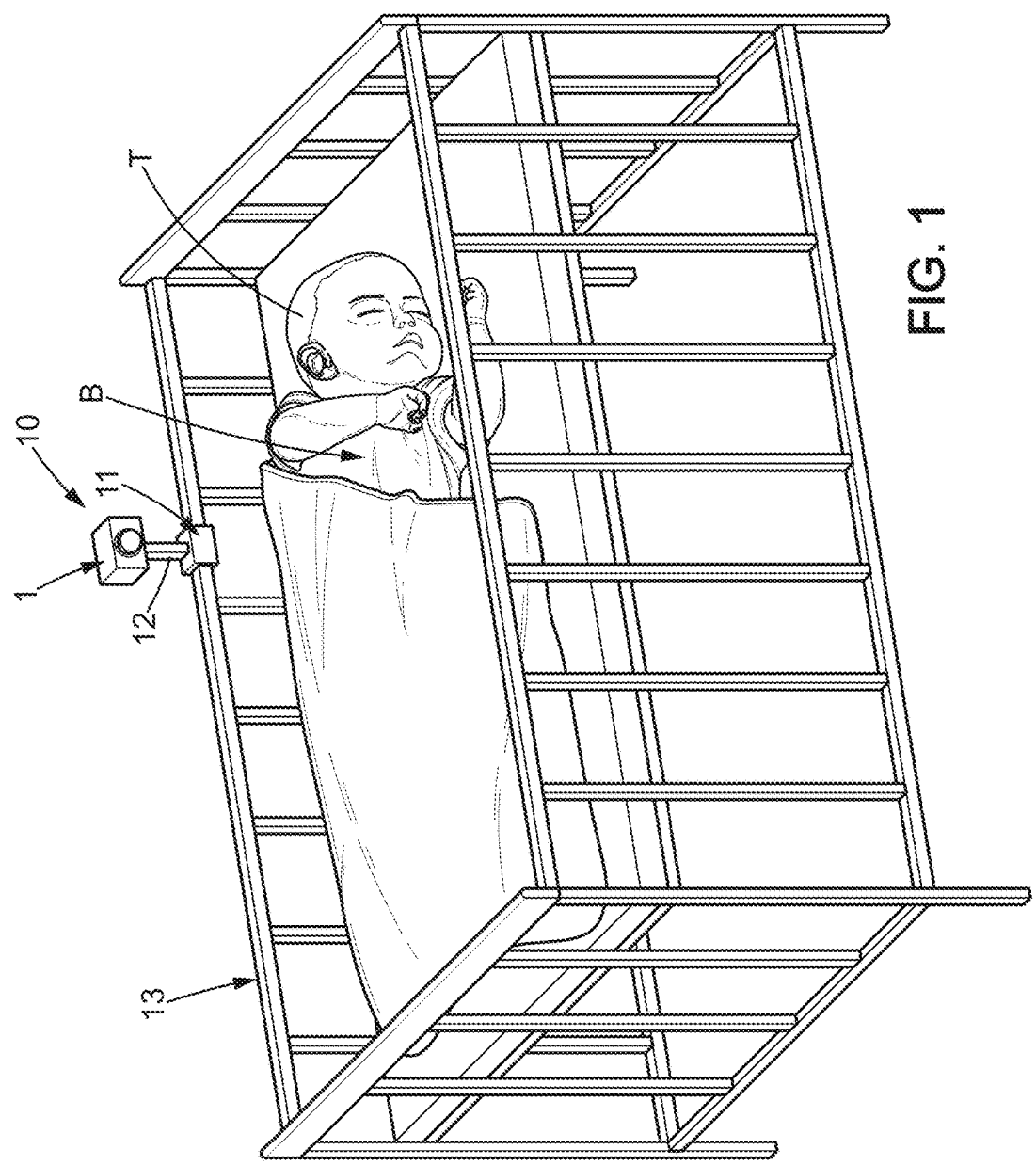
FIG. 1 is a general view of a crib containing a baby to be monitored by a method according to the invention.

FIG. 1 shows a baby B lying in a crib 13. In the context of the invention, baby is understood to mean an infant or child less than 10 years old. We are particularly interested in the case where the baby is placed in the crib for a nap or for the night. Typically, in this configuration, the general lighting in the room will be low or very low, referred to herein as dim or nocturnal conditions providing partial or total darkness.

In the example shown, a video monitoring system, denoted 10, comprises a video monitoring device 1 to be discussed in detail below, a mounting foot 12, and a mounting clamp 11. In the example shown, the mounting clamp is attached to a side rail of the crib or more generally of the bed. Note that in the monitoring assembly, it could also be secured to the crosspiece at the head or the foot of the bed.

Alternatively, the monitoring assembly may also be located elsewhere in the room.

The video monitoring device 1 may be attached to a different support, to a wall, to a bed canopy, etc.

Figure 2:
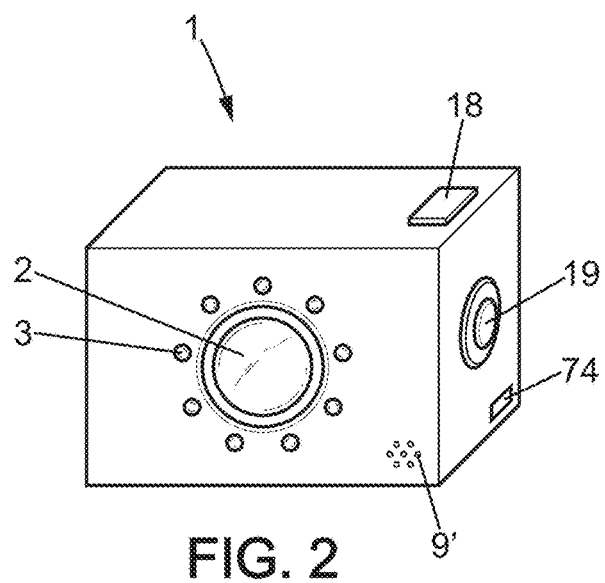
FIG. 2 is a view of the video monitoring device.
Figure 3:
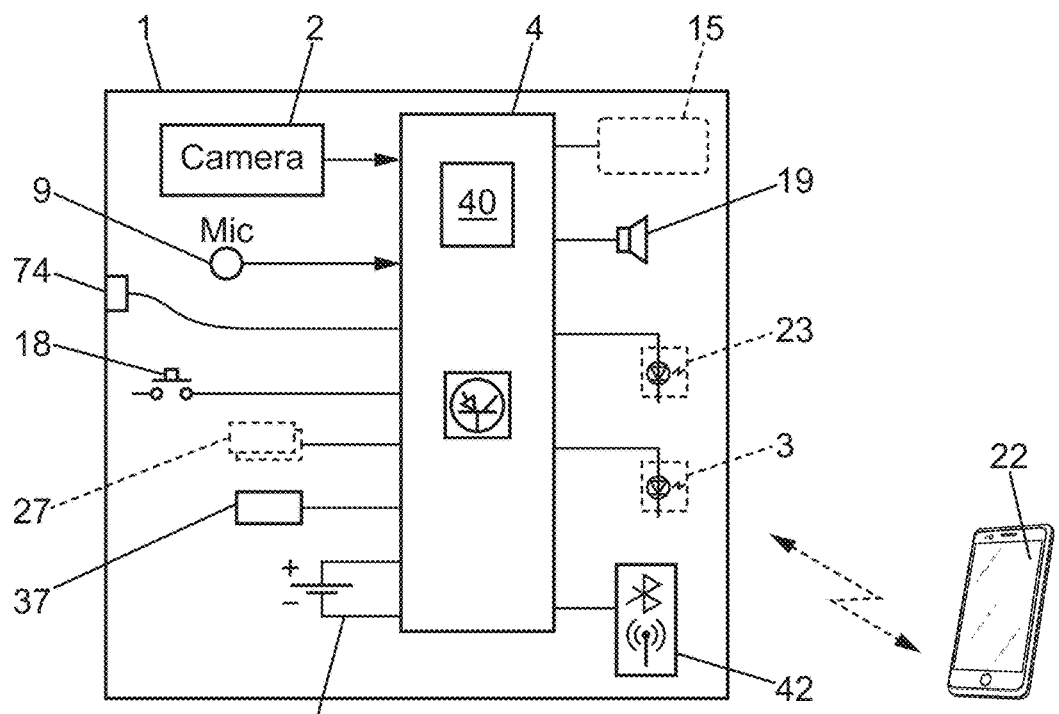
FIG. 3 shows a schematic block diagram of the device of FIG. 2.
Figure 4:
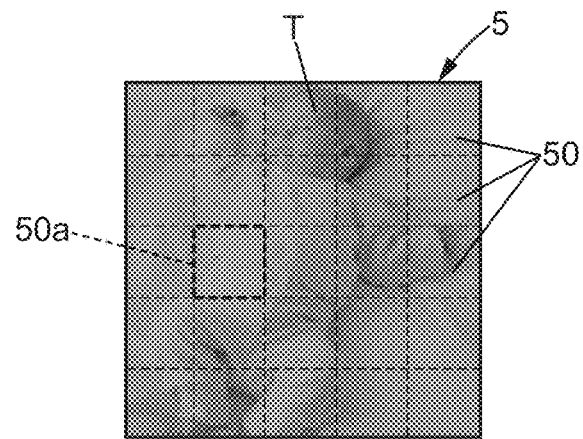
FIG. 4 represents a sample image captured by the camera.
Figure 5:
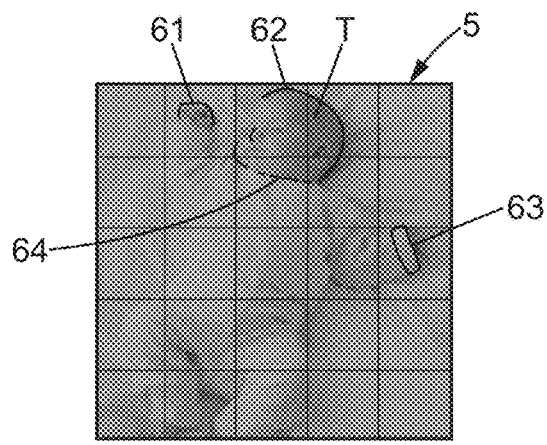
FIG. 5 illustrates the construction of edge segments.
Figure 6:
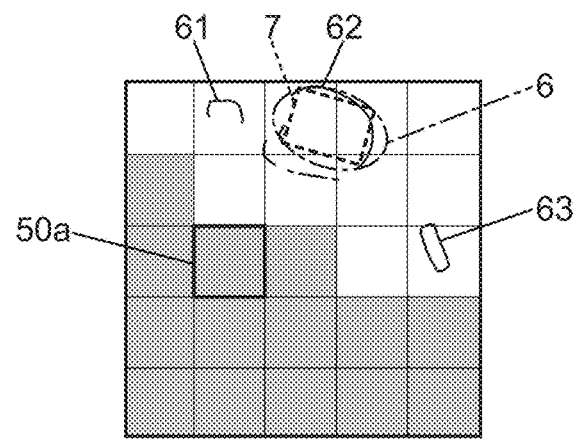
FIG. 6 illustrates the selection of an ellipse and of the area of interest.

As illustrated in more detail in FIG. 2, the video monitoring device 1 comprises a video camera 2, which has a wide viewing angle over a solid angle of at least 90° or more (110° or 135°) so that the camera can capture images of the entire relevant area of the crib or even the entire room of interest.

In addition, the monitoring device comprises light-emitting diodes 3 (LED) capable of emitting in the infrared band, thus forming a source of infrared light.

The video monitoring device 1 further comprises a computing unit 4 with a memory 40 as well as a battery 28 or alternatively a power supply unit connecting to the grid.

The video monitoring device 1 preferably also comprises a wireless communication interface 42 configured for exchanging data with a remote entity such as a smartphone 22.

The video monitoring device 1 may further comprise a microphone 9 for capturing sound, and a sound generator in the form of a small speaker 19.

In addition, there may be a light source 23 for dim atmospheric lighting whose intensity can be controlled by the monitoring device, an air quality sensor 37, and auxiliary sensors 27 for example for sensing temperature and/or humidity and/or air quality.

The video monitoring device 1 may further comprise one or more buttons 18, intended to be operated by a user (for example to configure the device, turn it on and turn it off) as well as a small display 15 for displaying states or parameters of the device (in which case the buttons 18 may be touch-sensitive).

The device may comprise a connector 74, and holes 9' near the bottom of the front face to improve pickup by the microphone. Holes 9' also favor sampling of ambient air for the purpose of air quality sensing as detailed below.

Advantageously according to the invention, the camera 2 periodically captures video images 5 of the baby B. The image capture frequency will be a few hertz or tens of hertz, preferably higher than 8 Hz. It should be noted that in the context of the invention the same camera is used to capture images in daylight and images in the dark.

An optical filter may be provided having two positions, i.e. a day position and a night position.

The device controls excitation of the infrared LEDs 3 either continuously or at times coinciding and consistent with the capture of images. The infrared LEDs are arranged so as to substantially illuminate the entire solid angle of view of the camera.

Advantageously in the case of baby monitoring, the method for image processing and analysis will seek to determine the position of the baby's head T.

To do so, a step of the method, denoted B1, consists of detecting edges or edge segments in one or more successive images captured by the camera.

For each image, spatial convolution with statistical thresholding is performed, or calculation of the correlation to the mean of the red component or of the configured mix of colors. This allows identifying and memorizing the curve portions 61,62,63,64 where the spatial gradient of the signal is the highest, corresponding in practice to edge segments within the image.

Identification of these edge segments can be confirmed by sequential analysis of several successive images; if similar edge segments are found at the same location in these multiple images, then the determination is confirmed.

Otherwise it may concern a macroscopic movement of the baby, a case which will be explained below.

When sequential analysis of several successive images has confirmed the presence of several edge segments, we proceed to the next step in which several edge segments are associated and together they are compared to an elliptical shape (ellipse) with which said several edge segments might match.

A relevance criterion is established for quantifying the correspondence of the combined edge segments 62,64 with the candidate ellipse.

Of course, if a continuous outline is found which forms a circle or a closed ellipse in the analyzed image, then the relevance criterion will assume the maximum value; but in practice often the image analysis only detects portions of the candidate ellipse, and the ellipse must be reconstructed and assigned a relevance criterion value.

This step, referenced B2, may in addition identify a plurality of candidate ellipses, in which case a selection filter is applied to the candidate ellipses to choose only one selected ellipse 6 coinciding with the outline of the baby's head T. This filter may use the size of the ellipse, the ratio of its major axis to minor axis, and also the proportion of the outline actually found in the previous step.

In the typical case of one head to be detected, the selection of such a selected ellipse 6 allows eliminating from the subsequent analysis all image areas outside of the ellipse, and defining an area of interest centered on the ellipse.

Once the area of interest has been determined, and subject to the baby making no significant movements (see below), then the step denoted C of the method is carried out, this step corresponding to a photoplethysmographic analysis intended to determine vital signs of the baby, particularly the heart rate HR but also the respiratory rate RR.

Advantageously, one can determine a first area of interest 7 for evaluating the heart rate (e.g. forehead), and a second area of interest that may be distinct from the first, for evaluating the respiratory rate.

Figure 7:
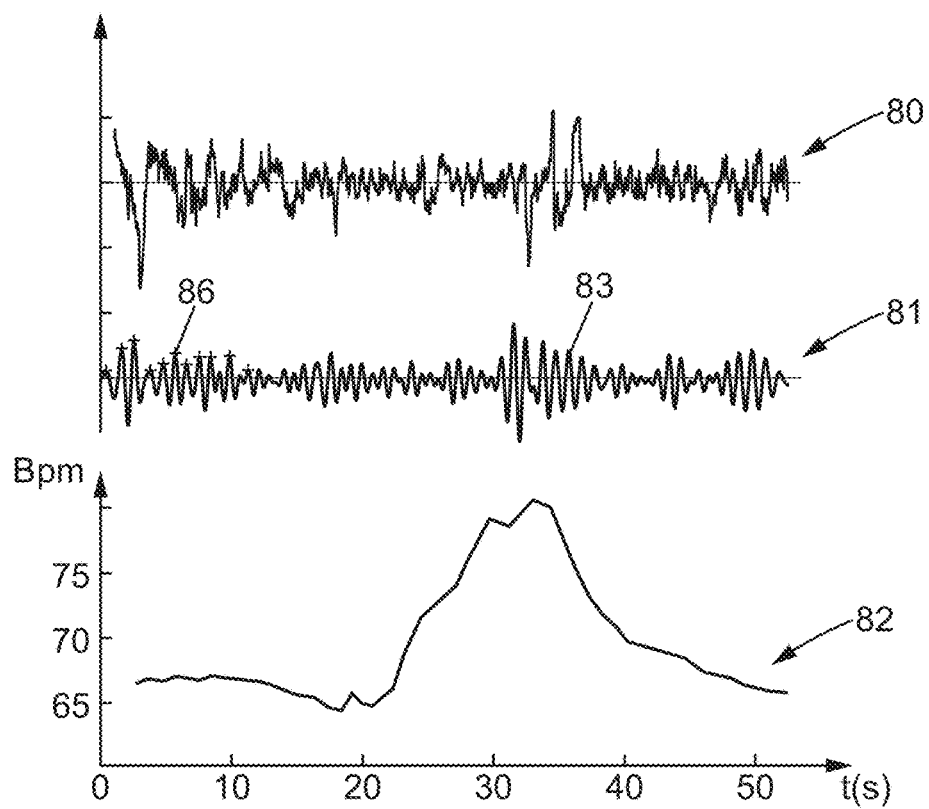
FIG. 7 illustrates an example of a filtered signal.

Preferably, for the heart rate determination, first there is applied to the light signal spatially averaged over the first area of interest, a sliding-window based offset calculation to eliminate the continuous component of the signal. This results in a signal denoted 80 in FIG. 7, which remains relatively noisy but no longer contains a continuous component.

Next, a digital filter with passband of 0.75 Hz-3.5 Hz is applied to the signal 80 in order to obtain a filtered signal 81. This eliminates spurious signals outside the frequency band of interest.

A peak detection step is then applied to the resulting filtered signal 81. This processing is intended to find the peaks 86 (only the first ones are indicated by crosses in FIG. 7).

The time interval between each consecutive peak 86 allows calculating the heart rate as illustrated in curve 82.

Optionally, a validity criterion relating to the relevance of the filtered signal 8 may be defined, to be used for selectively validating or not validating the heart rate information. This validity criterion may be based on the signal-to-noise ratio (S/N) of the signal 81.

A filtered and corrected signal is denoted 83.

If the heart rate value from step C satisfies the validity criterion, this value may be stored in memory and/or transmitted to a remote device 22 such as a smartphone connected by wireless link to the monitoring device 1.

Step C is carried out almost continuously, repeating periodically, for example obtaining a measurement every 5 seconds or every 10 seconds, knowing that to obtain each measurement, when appropriate, the device can increase the rate at which it captures images in the area of interest.

In parallel to step C, the method monitors that the baby is remaining substantially motionless, or in other words that the edge segments identified in step B1 remain substantially stable.

A special case is handled by the method according to the invention: when there is significant (macroscopic) movement of the baby. In this case, the baby's head moves, and the head's position must be determined again.

Detection of a significant movement of the baby can be achieved by analysis of the position of the edge segments and their evolution over successive images. Additionally or alternatively, the information provided by the microphone 9 can also be used, because a macroscopic motion of the baby will generate audio signals received by the microphone.

Those skilled in the art understand that a plethysmographic analysis cannot yield valid results when the baby is making significant movements.

However, it is arranged that the evolution of these movements are monitored (the step denoted D) in order to identify a return to a stable state where there is no significant movement by the baby, in which case steps B1-B2 are performed again, step C- of photoplethysmographic analysis being repeated with the new area of interest 7 established in step B2.

The abovementioned processing may be performed on the entire captured image 5. However, as a variant, the image may be subdivided to limit the computation resources required and the memory required. For example, the captured image 5 can be divided into an array of sub-images 50, each sub-image 50 being the same size to facilitate processing. In the illustrated example, the captured image is divided into 5×5 sub-images.

This has the advantage that certain images of flat or neutral content 50a (meaning with no significant variation in color or intensity over the area of the sub-image) can be eliminated during the edge detection in step B1. One criterion for eliminating the sub-images 50 of no interest can be based on a low light intensity and/or a low variation in the analyzed area.

Figure 8:
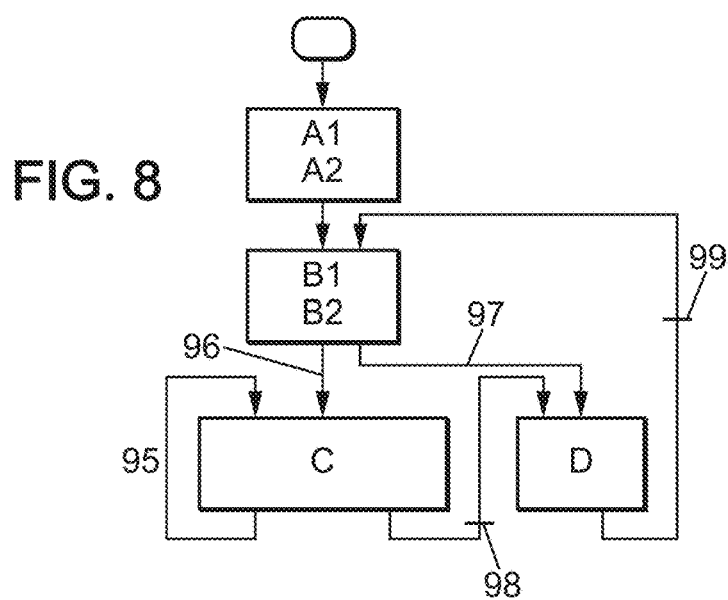
FIG. 8 shows a flowchart illustrating the method.

Now referring to FIG. 8, since steps B1-B2 have identified an area of interest, the transition 96 initializes the plethysmographic analysis (C-), and this is repeated (denoted 95) as long the baby is not moving. If the baby moves, then the plethysmographic analysis is suspended 97,98 and the step of monitoring the macroscopic movements (step D) puts the plethysmographic process on hold until a stable state is restored, illustrated by transition 99. Then the method restarts steps B1-B2, and then proceeds to step C-.

It should also be noted that the device installation does not require any special precautions, as automatic detection of the baby's head is possible even if the framing by the camera is not perfect relative to the crib.

It should be noted that the method for detecting the baby's head as disclosed above can also function in the daytime under natural lighting, and not only under dark illumination conditions.

The video monitoring device 1 further comprises a volatile organic compounds sensor 37 (known as a 'VOC' sensor). Such a sensor can detect several organic gases, such as butane, propane, octane, methanol, ethanol, propanol, butanol, and even aromatic compounds such as benzene, ethylbenzene, and toluene. The baby monitoring device may record the concentration of organic compounds during one or more periods of time, and send this information either in real time or in deferred mode to the smartphone 22.

Also the volatile organic compounds sensor 37 can detect hydrogen sulfide (H2S) concentration.

Regarding VOCs, some organic compounds can be released at home by cosmetics, cleaning products, fresh paint, new piece of furniture, they can include aldehydes, formaldehyde, methylene, toluene, acetone, butene, pentane, benzene or the like.

The VOC sensor 37 in question is an electrochemical MOS on-chip sensor. The sensing element comprises a metal oxide semiconductor layer reacting with VOCs by oxidation-reduction reactions. In the presence of a detectable gas, the conductivity of the metal-oxide semiconductor increases depending on the gas concentration in the air. A simple electrical circuit converts this conductivity into an output voltage which is measured. This voltage is then converted into a concentration level of VOCs in the room by the microcontroller. This conversion may be done by looking at a calibration look-up table, or by calculating a calibration function, and possibly after adjusting for other quantities provided by other sensors, for instance the temperature and/or humidity.

The VOC sensor 37 can alternatively be an ion detector using photoionization of the molecules in an air sample collected in the room where the baby's crib is located.

The VOC sensor 37 provides an aggregate level of organic compounds which combines all the organic compounds present.

Advantageously, the already mentioned humidity sensor 27 is used to compensate for the possible presence of water vapor in the sampled air and for correcting accordingly the sensed VOC concentration level.

Advantageously, since the VOC concentration level(s) is(are) transmitted to smartphone user, he/she can decide to ventilate/air the room in which the device is located. Furthermore, a VOC scale can be provided on a smartphone application to help the user decide whether it is required to ventilate/air the room.

Regarding the case of monitoring the baby, collected values of predefined period of time can be used to correlate the heart rate HR and/or respiratory rate RR with the VOC concentration levels in order to determine if the baby was affected by a certain level of VOCs at some time.

Figure 9:
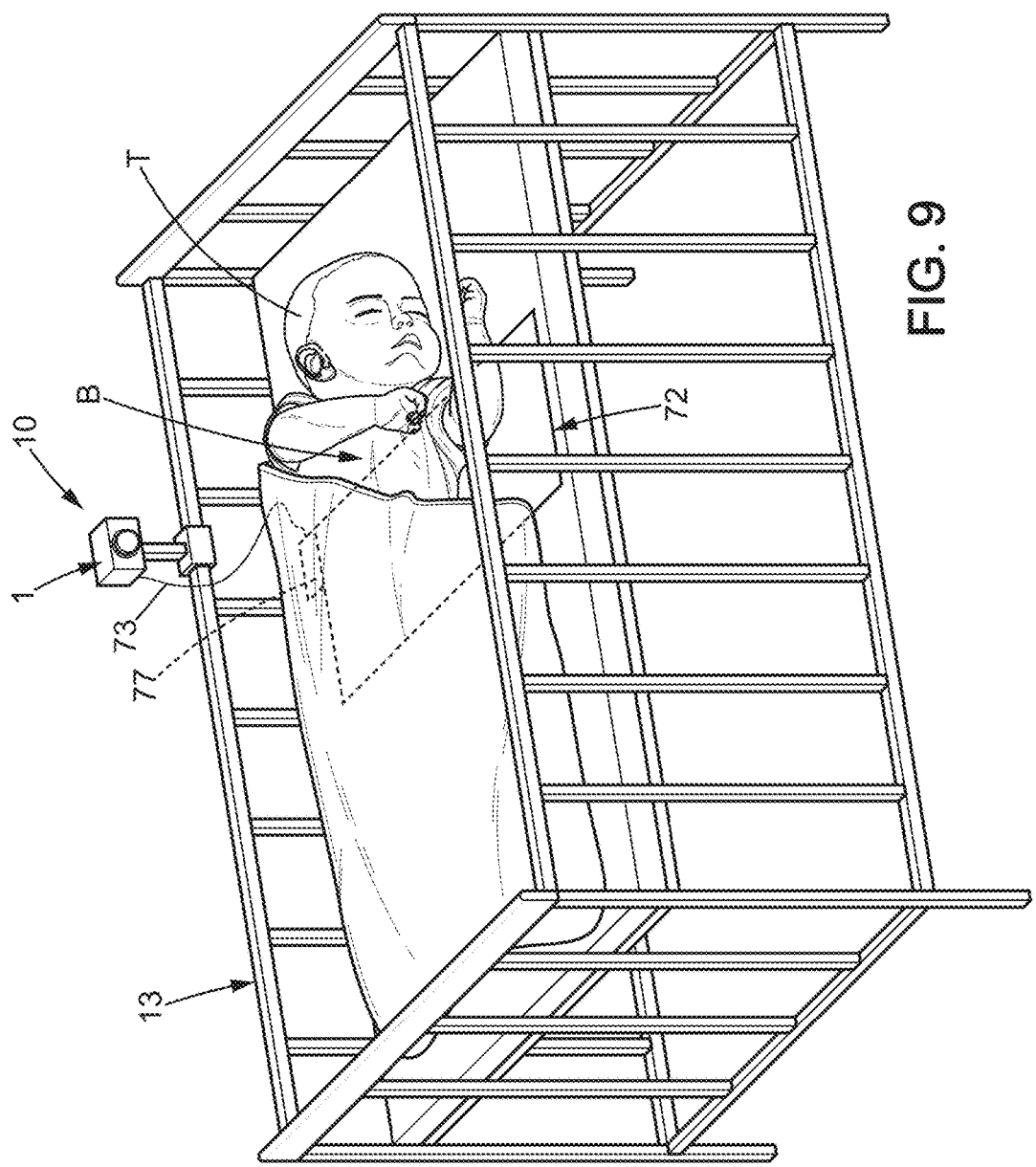
FIG. 9 illustrates a variant of the monitoring device with a detection sheet.

In addition, a detection sheet 72 may be provided that acts as a motion sensor, as shown in FIG. 9. This detection sheet 72 is installed on the mattress and the baby B is placed above it, in other words the detection sheet 72 is placed between the baby B and the mattress. The detection sheet may comprise a signal conditioning interface 77 and is connected to the monitoring device 1 by a flexible link 73, either electrical or pneumatic or a combination. This link 73 is connected to the device via the connector 74. The signal conditioning may be performed by the conditioning interface 77 or even directly wholly or in part by the monitoring device itself.

In the example illustrated, the detection sheet is formed by a thin air bladder, which allows detecting the baby's movements by ballistography.

To help the baby fall asleep more quickly and more easily, atmospheric lighting is provided by the atmospheric lighting means 23 and soft music through the speaker 19, both of them preferably decreasing in intensity.

To trigger the light and sound sequence, the beginning of the drowsiness phase can be detected by video determination of the heart rate as explained above. When the heart rate 82 slows and becomes more regular, then the control unit 4 triggers the light and sound sequence.

Alternatively, the computing unit uses not only the heart rate information but also the respiratory rate information detected for example by means of the microphone 9 and/or of said detection sheet 72. The computing unit 4 may also use video detection of movements of the baby's head T by means of the edge detection method as explained above.

When the computing unit 4 has triggered the sound and light sequence to assist with falling asleep and the baby starts to move about or to cry, then the sequence can be extended or restarted at the beginning.

If the sound and light sequence comes to an end with no change in the heart rate and with no movement of the baby, then the monitoring device turns the atmospheric lighting completely off and switches to night monitoring mode.

In a particular aspect, the video monitoring device can save the highlights of the day and/or night, in other words it can save images of events which occurred earlier; for example, based on detection of movement near the baby, saving images and audio whenever someone enters or leaves the room, and based on detection of crying, saving images and audio whenever the baby starts to cry, whenever there is a significant change in environmental parameters, whenever the baby smiles, etc.

According to a particular aspect, the video monitoring device can generate an alert sent to a remote device such as a smartphone or other device, upon detection of abnormal conditions such as environmental parameters exceeding preset thresholds, an unusually quiet or unusually restless environment, movement, pollution detection, etc.

Lastly, according to a particular aspect, the video monitoring device can be equipped with a two-way simultaneous audio connection, in other words a full-duplex connection, which allows the parent(s) and baby to exchange words or sound signals truly at the same time.

As a variant, instead of a baby, the video monitoring device can simply monitor what happens generally in a room of a home.

The invention claimed is:

1. A video monitoring device for monitoring air quality in a room of interest, comprising a computing unit, a camera, a communication interface, and a volatile organic compounds sensor configured to measure concentrations of organic compounds in the room of interest and to provide an aggregate concentration level of organic compounds which combines all the organic compounds present in the air of the room of interest, including butane, propane, octane, methanol, ethanol, propanol and butanol, and aromatic compounds including benzene, ethylbenzene, and toluene, said computing unit being configured to record the concentrations of organic compounds reported by the volatile organic compounds sensor, and configured to send images taken by the camera and volatile organic compounds concentrations to a remote entity of a user, so that the user can decide whether it is required to ventilate/air the room.

2. The video monitoring device according to claim 1, wherein the computing unit stores successive organic compound concentration level values in memory, for transmission at regular intervals to the remote entity.

3. The video monitoring device according to claim 1, wherein an alert threshold is provided in the computing unit, which allows to send immediately to the smartphone an alert message, as soon as the volatile organic compounds concentration level exceeds the predetermined alert threshold.

4. The video monitoring device according to claim 1, wherein the volatile organic compounds sensor is an electrochemical MOS on-chip sensor using oxidation-reduction reactions with gas(es) present in ambient air, whereby a volatile organic compounds concentration level can be measured.

5. The video monitoring device according to claim 1, wherein some vital signs of a baby, such as the heart rate and/or respiratory rate of the baby are evaluated by photoplethysmographic analysis of the captured images, thereby forming a device suitable for monitoring the baby in a room or in a crib.

6. The video monitoring device according to claim 1, further comprising a loudspeaker and a microphone, thereby forming two-way audio link, particularly suitable for interacting with a baby in a room or in a crib, remotely from a parent/caretaker using the smartphone.

7. A video monitoring system comprising a monitoring device according to claim 1, and a smartphone.

8. A method to monitor events in a room and an air quality in the room, the method comprising:
 measuring a concentration of organic compounds in a room with a volatile organic compounds sensor
 taking images of at least part of the room,
 storing the organic compound concentration data in a memory of a computing unit,
 send images taken by the camera and volatile organic compounds concentrations, from the computing unit to a remote entity such as a smartphone over a wireless link, and
 decide whether it is required to ventilate/air the room.

9. The method to according to claim 8, wherein the transmission to the smartphone occurs at regular intervals.

10. The method to according to claim 8, wherein an alert threshold is provided in the computing unit, the method further comprising:
 sending quickly to the smartphone an alert message, as soon as the volatile organic compounds concentration exceeds the predetermined alert threshold.

11. A video monitoring device for monitoring air quality in a room of interest, comprising a computing unit, a camera, a communication interface, and a volatile organic compounds sensor configured to measure concentrations of organic compounds in the room of interest and to provide an aggregate concentration level of organic compounds which combines all the organic compounds present in the air of the room of interest, including butane propane, octane, methanol, ethanol, propanol, butanol, and aromatic compounds including benzene, ethylbenzene, and toluene, said volatile organic compounds sensor being arranged within the video monitoring device, said computing unit being configured to record the concentrations of organic compounds reported by the volatile organic compounds sensor, and configured to send images taken by the camera and volatile organic compounds concentrations to a remote entity.

* * * * *